United States Patent
Kerns et al.

(10) Patent No.: US 7,449,092 B2
(45) Date of Patent: Nov. 11, 2008

(54) DUAL MODE OXYGEN SENSOR

(75) Inventors: James M. Kerns, Trenton, MI (US); Harry Burleson, Waterford, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 893 days.

(21) Appl. No.: 10/740,115

(22) Filed: Dec. 17, 2003

(65) Prior Publication Data

US 2005/0133381 A1   Jun. 23, 2005

(51) Int. Cl.
*G01N 27/409* (2006.01)
*G01N 27/41* (2006.01)

(52) U.S. Cl. .................. 204/425; 204/406; 73/23.32
(58) Field of Classification Search .............. 204/424, 204/425, 426, 406; 205/783.5; 76/23.32
See application file for complete search history.

(56) References Cited

U.S. PATENT DOCUMENTS

| | | | | |
|---|---|---|---|---|
| 4,384,935 A | * | 5/1983 | De Jong | 204/406 |
| 4,718,999 A | * | 1/1988 | Suzuki et al. | 204/406 |
| 4,915,080 A | * | 4/1990 | Nakaniwa et al. | 123/691 |
| 5,209,206 A | * | 5/1993 | Danno et al. | 123/479 |
| 5,340,462 A | * | 8/1994 | Suzuki | 204/425 |
| 5,391,284 A | * | 2/1995 | Hotzel | 204/425 |
| 5,413,683 A | | 5/1995 | Murase et al. | |
| 5,474,665 A | | 12/1995 | Friese et al. | |
| 5,833,836 A | * | 11/1998 | Takami et al. | 205/785 |
| 5,972,200 A | | 10/1999 | Kim | |
| 6,018,945 A | | 2/2000 | Nakagawa | |
| 6,482,310 B2 | * | 11/2002 | Detwiler et al. | 205/784.5 |
| 2001/0052473 A1 | | 12/2001 | Ohkuma | |
| 2002/0020393 A1 | * | 2/2002 | Ogawa et al. | 123/406.26 |

* cited by examiner

*Primary Examiner*—Kaj K Olsen
(74) *Attorney, Agent, or Firm*—Allan J. Lippa; Alleman Hall McCoy Russell & Tuttle, LLP

(57) ABSTRACT

An oxygen sensor for measuring exhaust gases of an internal combustion engine is described. The sensor provides an output that has a high gain near the stoichiometric air-fuel ratio, and a lower gain in the lean and rich air-fuel ratio regions. Further, the sensor provides wide range air-fuel ratio signal to be used in engine feedback control.

9 Claims, 8 Drawing Sheets

DUAL MODE OXYGEN SENSOR

TECHNICAL FIELD

The field of the invention relates to an exhaust gas oxygen sensor used in engines of mobile vehicles to reduce emissions during a wide range of operating conditions.

BACKGROUND AND SUMMARY OF THE INVENTION

Engine exhaust systems utilize sensors to detect operating conditions and adjust engine air-fuel ratio. One type of sensor used is a switching type heated exhaust gas oxygen sensor (HEGO). The HEGO sensor provides a high gain between measured oxygen concentration and voltage output. The HEGO can provide an accurate indication of the stoichiometric point, but provides air/fuel information over an extremely limited range (other than indicating lean or rich).

Another type of sensor used is a universal exhaust gas oxygen sensor (UEGO). The UEGO sensor can operate across a wide range of air-fuel ratios, for example from 10:1 (rich) to pure air (lean). However, as a result, the voltage to oxygen concentration has a lower gain. Furthermore, the UEGO sensor may not provide an indication of stoichiometry as precise as the HEGO sensor, especially under widely varying temperature conditions.

The inventors herein have recognized that when an oxygen sensor is used in a post catalyst position, the precise indication of stoichiometry given by the HEGO sensor provides advantageous results, but the limited bandwidth degrades the capability of the control system to provide fast convergence to desired operating conditions. Likewise, using an UEGO sensor can provide advantageous information when operating away from stoichiometry, however, catalyst efficiency when operating about stoichiometry can degrade due to the imprecise measurement of the stoichiometric point.

One approach to try and correct for the UEGO sensor inaccuracies near stoichiometry is described in U.S. Publication 2001/0052473. Here, the power supply to the pump current is cut off, and a correction value is then determined. However, the inventors herein have also recognized a disadvantage with such an approach. For example, the power supply can be turned off only in limited conditions, such as deceleration fuel shut-off, and thus an accurate reading of stoichiometry is only available under select conditions. Furthermore, the select conditions typically do not include operation at stoichiometry under feedback control. As such, the measurement comes at an inappropriate time and is not available when needed most. Further, errors due to variations in temperature can change depending on engine conditions, and as such even if this correction is used, errors persist.

To overcome these disadvantages, and harness the respective advantages of the above sensors, the following approach can be utilized. Specifically, in one aspect, a sensor is used that comprises: a first reference cell having a reference voltage; a second pumping cell having a pumping current, and a circuit configured to pump current in the pumping cell in a first direction to prevent the reference voltage from increasing higher than a first voltage limit; and to pump current in the pumping cell in a second direction to prevent the reference voltage from decreasing lower than a second voltage limit. In one example, when the circuit pumps current in the pumping cell in the first direction to prevent the reference voltage from increasing higher than the first voltage limit, the circuit allows the reference voltage to decrease lower than the first voltage limit. Likewise, when the circuit pumps current in the pumping cell in the second direction to prevent the reference voltage from decreasing lower than the second voltage limit, the circuit allows the reference voltage to increase higher than the second voltage limit.

In this way, the reference voltage can be driven by chemical reactions to equilibrate and provide an accurate indication of stoichiometry, similar to a HEGO sensor. Likewise, outside of stoichiometry, the reference voltage is controlled in a one-sided fashion via positive and negative pumping current at respective voltage limits to provide an indication of air-fuel ratio over a wide range.

An advantage of such operation is the ability to provide a signal that is both accurate at stoichiometry and indicative of air-fuel ratio over a wider range. Such operation leads to more accurate feedback air-fuel ratio control at stoichiometry with high gain sensing, while still providing air-fuel feedback information outside of stoichiometry, such as for lean burn operation.

In another aspect, a method is provided for sensing an air-fuel ratio of exhaust gasses from an engine using a sensor having a pumping cell and a reference cell. The method comprises:

pumping current in the pumping cell during at least a first set of operating conditions;

reducing said pumping during at least a second set of operating conditions;

providing a signal from said sensor during at least said first and second operating conditions; and adjusting at least one of a fuel injection amount and an air amount into the engine to maintain a desired air-fuel ratio based on said signal during at least said first and second operating conditions.

As such, the method advantageously uses a sensor that both (1) pumps current in the pumping cell during at least a first set of operating conditions (such as to provide an indication of air-fuel ratio over a wide range), and (2) reduces said pumping during at least a second set of operating conditions (such as about stoichiometry to allow chemical equilibrium to drive a reference voltage). In this way, by using a signal from the sensor in both circumstances to provide feedback air-fuel ratio control, accurate control can be obtained both about stoichiometry, and away from stoichiometry. Increased catalyst efficiency and reduced emissions can also be obtained.

BRIEF DESCRIPTION OF THE DRAWINGS

The advantages described herein will be more fully understood by reading example embodiments in which the invention is used to advantage, referred to herein as the Description of Embodiment(s), in which like reference numbers indicate like features, with reference to the drawings wherein.

DESCRIPTION OF EMBODIMENT(S)

Figure 1:
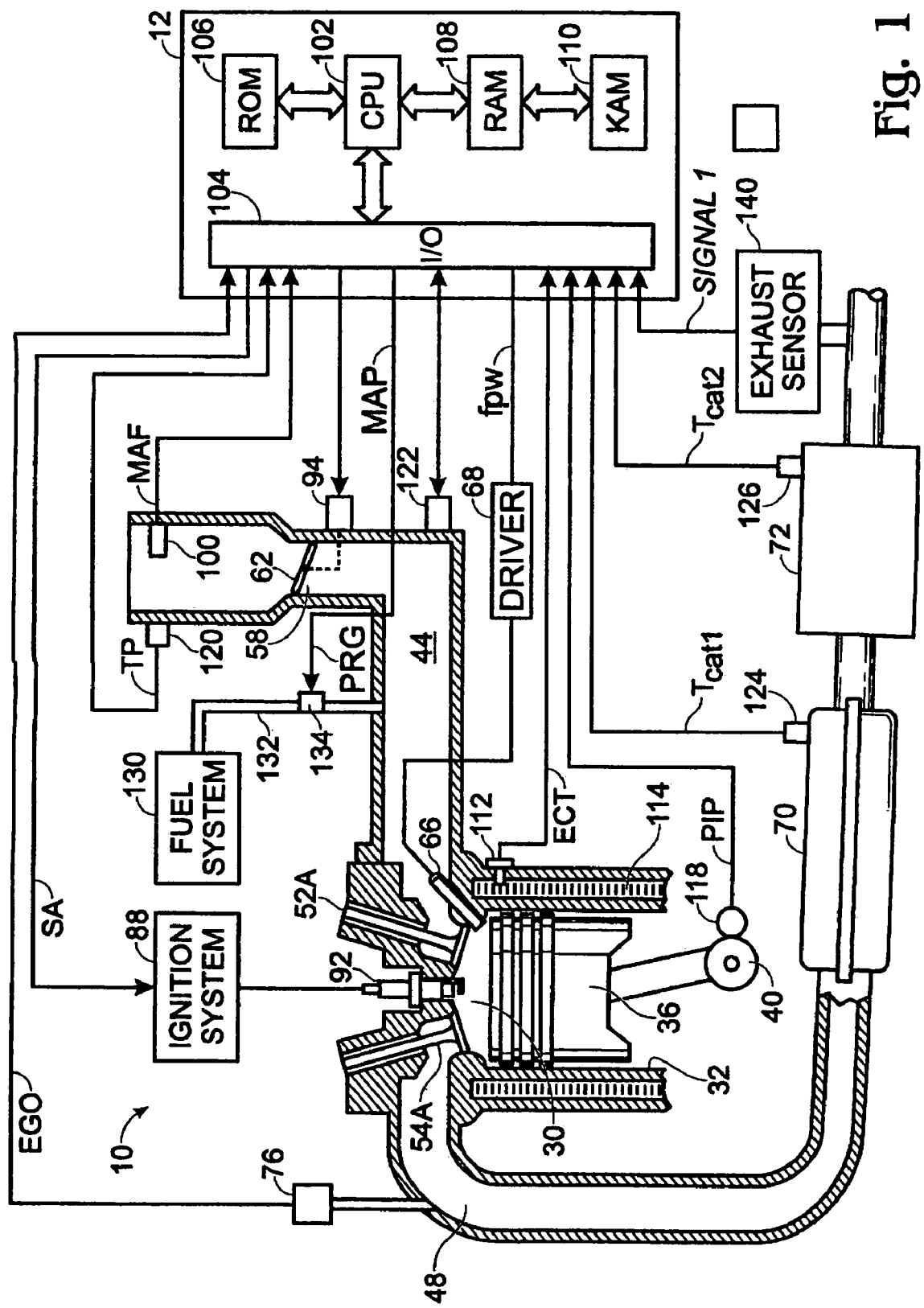
FIG. 1 is a block diagram of an engine utilizing an exhaust gas sensor to advantage.

Direct injection spark ignited internal combustion engine 10, comprising a plurality of combustion chambers, is controlled by electronic engine controller 12 as shown in FIG. 1. Combustion chamber 30 of engine 10 includes combustion chamber walls 32 with piston 36 positioned therein and connected to crankshaft 40. In this particular example, piston 30 includes a recess or bowl (not shown) to help in forming stratified charges of air and fuel. Combustion chamber 30 is shown communicating with intake manifold 44 and exhaust manifold 48 via respective intake valves 52a and 52b (not shown), and exhaust valves 54a and 54b (not shown). Fuel injector 66 is shown directly coupled to combustion chamber 30 for delivering liquid fuel directly therein in proportion to the pulse width of signal fpw received from controller 12 via conventional electronic driver 68. Fuel is delivered to fuel injector 66 by a conventional high pressure fuel system (not shown) including a fuel tank, fuel pumps, and a fuel rail.

Intake manifold 44 is shown communicating with throttle body 58 via throttle plate 62. In this particular example, throttle plate 62 is coupled to electric motor 94 so that the position of throttle plate 62 is controlled by controller 12 via electric motor 94. This configuration is commonly referred to as electronic throttle control (ETC), which is also utilized during idle speed control. In an alternative embodiment (not shown), which is well known to those skilled in the art, a bypass air passageway is arranged in parallel with throttle plate 62 to control inducted airflow during idle speed control via a throttle control valve positioned within the air passageway.

Exhaust gas oxygen sensor 76 is shown coupled to exhaust manifold 48 upstream of emission control device 70. In this particular example, sensor 76 provides signal EGO, which indicates whether exhaust air-fuel ratio is either lean of stoichiometry or rich of stoichiometry. Signal EGO is used to control engine air-fuel ratio as described in more detail below. In an alternative embodiment, sensor 76 provides signal UEGO to controller 12, which can convert signal UEGO into a relative air-fuel ratio λ (air-fuel ratio relative to the stoichiometric air-fuel ratio, so that a value of 1 is the stoichiometric, with a value less than one indicating rich, and a value greater than one indicating lean). Signal UEGO is used to advantage during feedback air-fuel ratio control in a manner to maintain average air-fuel ratio at a desired air-fuel ratio. Further, sensor 76 can be a sensor as described below in FIG. 3 or 4 which provides a high gain signal at stoichiometry as well as a wide range air-fuel ratio signal.

Conventional distributorless ignition system 88 provides ignition spark to combustion chamber 30 via spark plug 92 in response to spark advance signal SA from controller 12.

Controller 12 causes combustion chamber 30 to operate in either a homogeneous air-fuel ratio mode or a stratified air-fuel ratio mode by controlling injection timing. In the stratified mode, controller 12 activates fuel injector 66 during the engine compression stroke so that fuel is sprayed directly into the bowl of piston 36. Stratified air-fuel ratio layers are thereby formed. The strata closest to the spark plug contain a stoichiometric mixture or a mixture slightly rich of stoichiometry, and subsequent strata contain progressively leaner mixtures. During the homogeneous mode, controller 12 activates fuel injector 66 during the intake stroke so that a substantially homogeneous air-fuel ratio mixture is formed when ignition power is supplied to spark plug 92 by ignition system 88. Controller 12 controls the amount of fuel delivered by fuel injector 66 so that the homogeneous air-fuel ratio mixture in chamber 30 can be selected to be substantially at (or near) stoichiometry, a value rich of stoichiometry, or a value lean of stoichiometry. Operation substantially at (or near) stoichiometry refers to conventional closed loop oscillatory control about stoichiometry. The stratified air-fuel ratio mixture will always be at a value lean of stoichiometry, the exact air-fuel ratio being a function of the amount of fuel delivered to combustion chamber 30. An additional split mode of operation wherein additional fuel is injected during the exhaust stroke while operating in the stratified mode is available. An additional split mode of operation wherein additional fuel is injected during the intake stroke while operating in the stratified mode is also available, where a combined homogeneous and split mode is available.

Second emission control device 72 is shown positioned downstream of device 70. Devices 70 and 72 can be various types of emission control devices. As shown in FIG. 2, each device can contain multiple catalyst bricks (70A, 70B, and so on; 72A, 72B, and so on). Alternatively, each can contain a single catalyst brick. In yet another example, the devices can contain just one, two, or three bricks each. Additionally, various types of catalytic converters can be used, such a three-way catalytic washcoats. For example, three way catalysts that absorb NOx when engine 10 is operating lean of stoichiometry can be used. In such catalysts, the absorbed NOx is subsequently reacted with rich exhaust gas constituents (HC and CO, for example) and catalyzed during a NOx purge cycle when controller 12 causes engine 10 to operate in either a rich mode or a near stoichiometric mode.

Controller 12 is shown in FIG. 1 as a conventional microcomputer including: microprocessor unit 102, input/output ports 104, an electronic storage medium for executable programs and calibration values, shown as read-only memory chip 106 in this particular example, random access memory 108, keep alive memory 110, and a conventional data bus.

Controller 12 is shown receiving various signals from sensors coupled to engine 10, in addition to those signals previously discussed, including: measurement of inducted mass air flow (MAF) from mass air flow sensor 100 coupled to throttle body 58; engine coolant temperature (ECT) from temperature sensor 112 coupled to cooling sleeve 114; a profile ignition pickup signal (PIP) from Hall effect sensor 118 coupled to crankshaft 40 giving an indication of engine speed (RPM); throttle position TP from throttle position sensor 120; and absolute Manifold Pressure Signal MAP from sensor 122. Engine speed signal RPM is generated by controller 12 from signal PIP in a conventional manner and manifold pressure signal MAP provides an indication of engine load.

In this particular example, temperatures Tcat1 and Tcat2 of devices 70 and 72 are inferred from engine operation. In an alternate embodiment, temperature Tcat1 is provided by temperature sensor 124 and temperature Tcat2 is provided by temperature sensor 126.

Fuel system 130 is coupled to intake manifold 44 via tube 132. Fuel vapors (not shown) generated in fuel system 130 pass through tube 132 and are controlled via purge valve 134. Purge valve 134 receives control signal PRG from controller 12.

Figure 3:
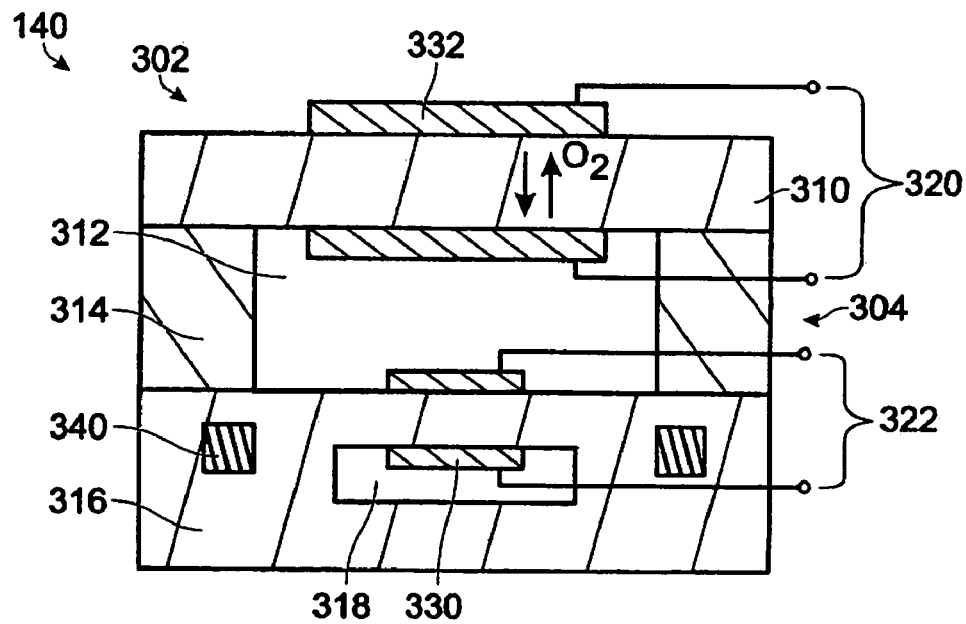
FIGS. 3 and 4 show a schematic of dual cell sensor 140.

In one example, exhaust sensor 140 is a second EGO type exhaust gas oxygen sensor that produces output signal (SIGNAL1). In an alternative example, sensor 140 can be a UEGO sensor. Finally, in still another example, sensor 140 is a sensor as described below with regard to FIG. 3 or 4. For example, if the sensor of FIG. 3 is used, then two output signals may be provided to controller 12. Alternatively, signal 1 can be $V_{out}$ from FIGS. 6 and 7, for example.

While FIG. 1 shows a direct injection engine, a port fuel injection engine, where fuel is injected through a fuel injector in intake manifold 44, can also be used. Engine 10 can be operated homogeneously substantially at stoichiometry, rich of stoichiometry, or lean of stoichiometry.

Those skilled in the art will recognize, in view of this disclosure, that the methods described below can be used to advantage with either port fuel injected or directly injected engines.

Note also, that in one example, devices 70 and 72 are three-way catalysts.

Figure 2A:
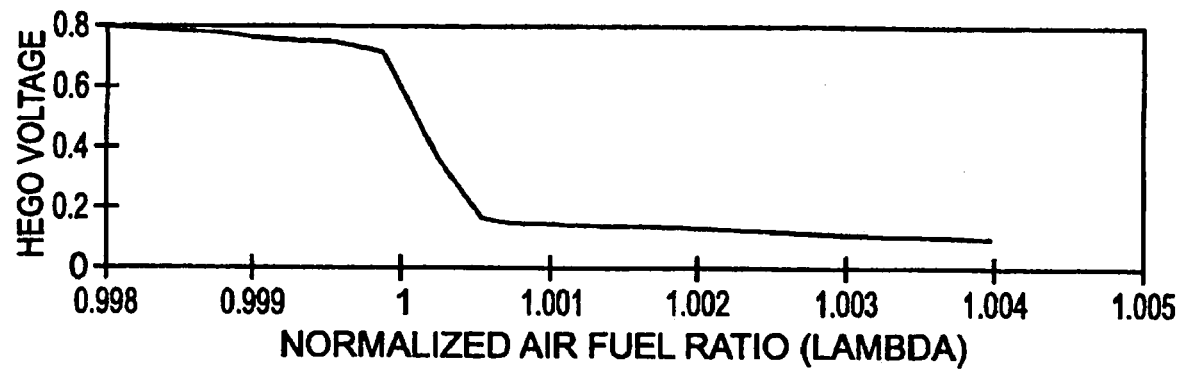
FIGS. 2A and 2B are graphs showing example outputs of an HEGO sensor and a UEGO sensor, respectively.
Figure 2B:
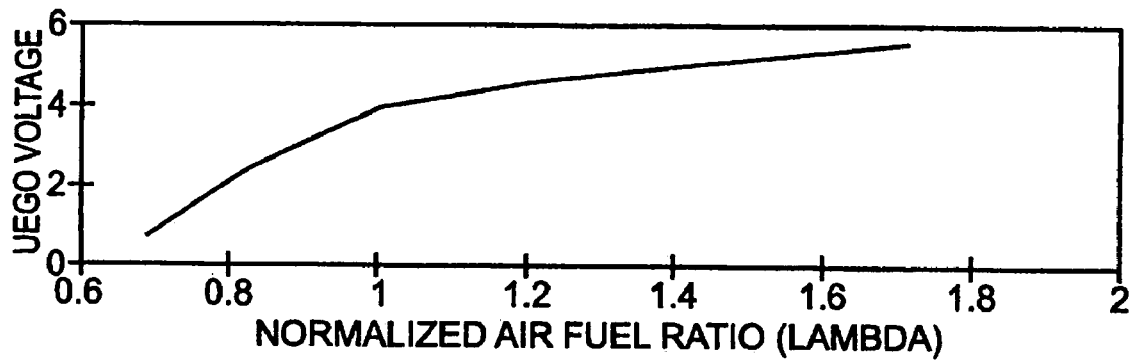

Referring now to FIGS. 2A and 2B, a description is given for two types of exhaust gas oxygen sensors that are used in the automotive industry; a switching (HEGO) sensor and a wide range (UEGO) sensor. The HEGO sensor provides a high gain and operates close to stoichiometry but provides air/fuel information over a limited range. The UEGO sensor operates across a wide range of air fuel ratios; typically from 10:1 to air, but as a result has a lower gain. And, the UEGO sensor does not provide as precise an indication of stoichiometry as the HEGO sensor. Dual cell UEGO sensors measure the air fuel ratio by measuring the oxygen pumping current required to maintain a stoichiometric air fuel ratio in a cavity inside the sensor as measured by an internal HEGO like reference circuit. FIG. 2A shows an example HEGO sensor response, and FIG. 2B shows an example UEGO sensor response. As discussed above, while each of these sensors has its advantages, each also has its disadvantages.

For example, when a sensor is used in a post catalyst position, the precise indication of stoichiometry given by the HEGO sensor is useful, but the limited bandwidth limits the capability of the control system. Further, the limited range of accurate information also limits use away from stoichiometric operation (such as during feedback lean air-fuel ratio, or rich air-fuel ratio, control).

To overcome at least some of these disadvantages, in one example, a method for controlling a sensor having at least two cells to provide a HEGO-like signal at stoichiometry and a UEGO-like signal at air fuel ratios away from stoichiometry is described. For example, as described in more detail below, by turning the pumping current off at stoichiometry and providing a signal that blends the output of both the reference and pumping circuit, such a result is possible.

Referring now to FIG. 3, a portion of sensor 140 is described in more detail. Specifically, oxygen pumping cell 302 is shown with a solid electrolyte material 310, such as zirconia. Pump electrode pair 332 is shown mounted to solid electrolyte material 310. The electrodes can be of various types, such as platinum, and provide a pumping current 320, creating a flow of oxygen molecules depending on the direction of current.

Reference cell 304 is formed via substrate 316 comprised also of a solid electrolyte material such as zirconia (ZrO2) having electrode pair 330. Air is introduced via hole (or reference cavity) 318, and an electrode pair 330 is also shown. A porous diffusion passage 314 is coupled between substrate 310 and 316, creating the hollow reference chamber (or detection cavity) 312. A reference voltage 322 is provided via the electrode pair 330. Note that a heater 340 for heating the sensor can be added, if desired.

As shown, the detection cavity is exposed to the exhaust gasses via the diffusion passage. In this system, in a first range, the a dual cell sensor measures the air-fuel ratio via the oxygen pumping current required to maintain a stoichiometric air fuel ratio in the cavity 312 inside the sensor as measured by an internal reference voltage 322. Specifically, the sensing cell reacts to the air-fuel ratio of the detection cavity and is used to control the pumping cell that will then pump oxygen in or out of the detection cavity. By controlling the pumping cell such that the reference cell maintains a constant voltage (typically 0.45) the pumping current will then correlate to the air fuel ratio of the exhaust gasses. For example, an interface circuit that measures the pumping current and creates a signal that can be measured by a powertrain control module (see FIG. 1) can be used.

However, rather than using the pumping cell to hold reference cell to a fixed voltage under all conditions, the pumping cell is used to keep the reference cell voltage from exceeding pre-determined upper and lower limits in a one-sided control fashion. When the reference cell is within these limits, the reference voltage is used as an accurate, high gain air/fuel indication. At the limits, when the pumping is active, the pumping current is used to indicate the air fuel ratio across a significantly wider range.

Thus, rather than controlling the reference cell to a fixed voltage and relying on the measurement of the pumping current to indicate air fuel ratio under all conditions, one of the example methods described herein allows the reference cell to float within some range and uses both the reference cell voltage and pumping current (when active) to indicate the air-fuel ratio. This provides both the high accuracy and high gain of the HEGO sensor at stoichiometry and the wide range capability of the UEGO sensor into a single output signal.

One reason for this increased accuracy is that when the pumping cell is not active, i.e., the reference voltage is within selected limits, the output signal is driven my chemical equilibrium reactions, and thus has reduced sensitivity to external factors, such as exhaust temperature, etc. However, when the pumping cell is active to maintain the reference voltage at either the upper (lean) limit or the lower (rich) limit, an indication of air-fuel ratio over a wide range can be achieved.

Figure 4:
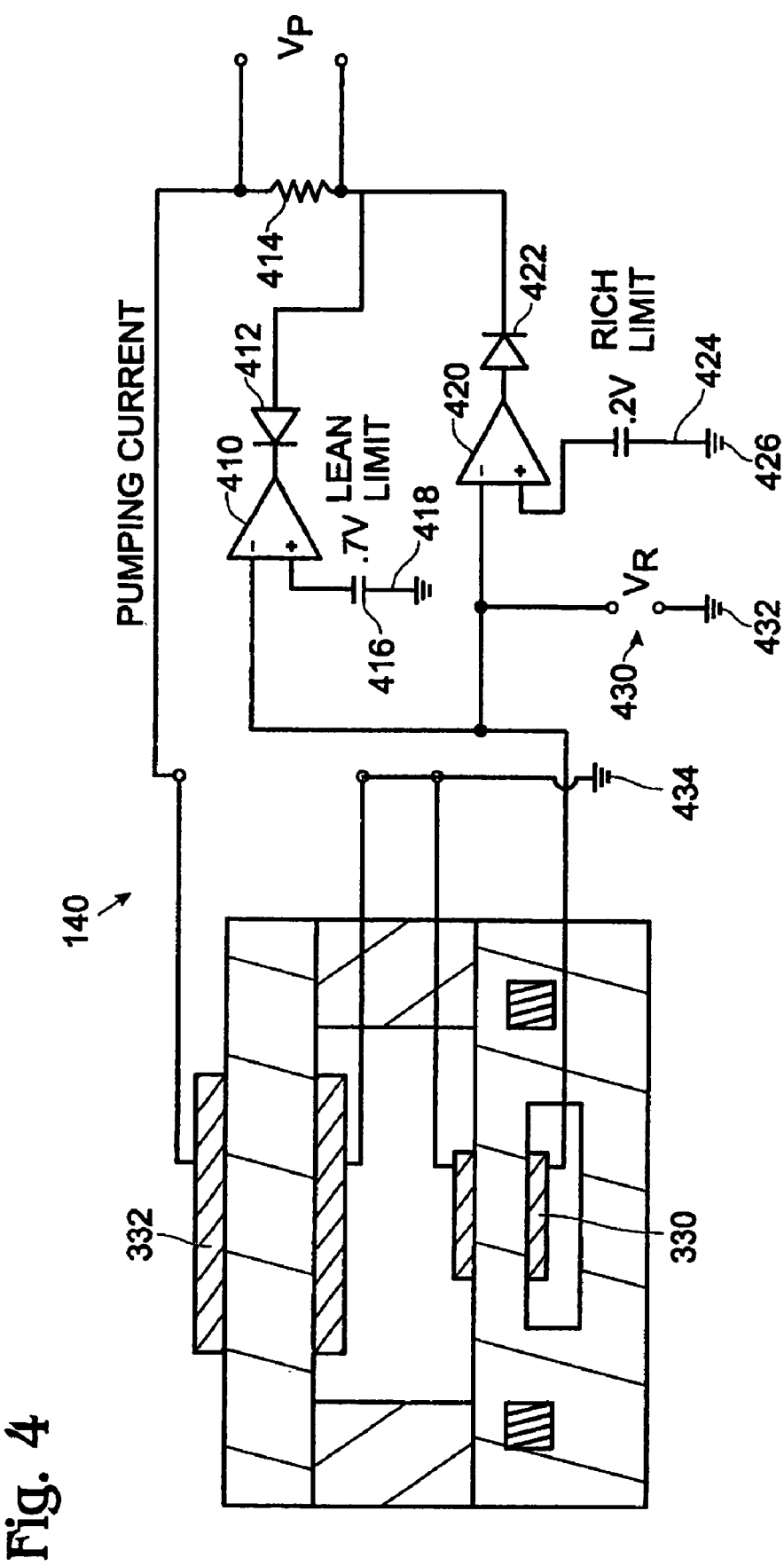

FIG. 4 shows sensor 140 having an example circuit for processing the reference voltage and controlling pumping current.

The circuit is shown coupled to electrodes 330 and 332 and sensor 140. The output of the internal electrode of 332 is coupled to ground 434. The outer electrode of 332 is coupled to resister 414 and generates voltage output ($V_p$) across it. In addition, operational amplifier 410 is shown with the negative terminal coupled to the inner electrode 330. The positive terminal of amplifier 410 is coupled to ground 418 via the 0.7 volt source. The 0.7 volt source represents an example upper voltage limit, which is set as the lean limit in this example. However, various other voltage levels can also be used, including a variable voltage level changing based on operating conditions. The output of operational amplifier 410 is coupled through a diode 412 to resistor 414.

Continuing with the circuit shown in FIG. 4, operational amplifier 420 is also shown with the negative terminal coupled to the inner electrode of 330. The negative electrode of operational amplifier 420 is also read out through the voltage ($V_r$) 430, which is then coupled to ground 432. The voltage output ($V_r$) 430 represents a reading of the reference voltage for the reference cell of sensor 140. Operational amplifier 420 is also shown with the positive terminal coupled to ground 426 through the 0.2 voltage source 424. The 0.2 voltage source represents a rich limit value, and as described above with regard to the 0.7 voltage limit value of 416, this is just one example value for this lower limit. The output of 420 is shown coupled to 422 pumped voltage output ($V_p$). Note that the diode 412 and the diode 420 are shown coupled in opposite directions. This illustrates how the one-sided control of voltage at the limit value is accomplished with a relatively simple circuit.

Various other circuits can be used to perform the desired acts and operations, or add additional signal conditioning and modification.

This shows an example outline of the proposed control circuit. When the reference cell voltage is between the 0.2 volt and 0.7 volt limits, neither of the control circuits will supply pumping current (or will supply a reduced current), and the reference cell voltage ($V_r$) can be used as the sensor output. When the reference cell voltage reaches 0.2 volts (indicating a slightly rich mixture), the lower amplifier will be able to provide the pumping current necessary pump oxygen into the detection cavity to hold the reference cell at 0.2 volts. This is an example of one-sided control since the circuit will not prevent the voltage from increasing past 0.2 volts. The air fuel ratio measurement would then be derived from the pumping current output ($V_p$). Conversely when the reference voltage reaches the 0.7 volt limit, the upper amplifier will generate the required pumping current to maintain the reference voltage at 0.7 volts. However, this is also an example of one-sided control (although in the opposite direction) since the circuit will not prevent the voltage from decreasing below 0.7 volts.

As shown above, the circuit has two separate outputs, $V_p$ and $V_r$. An alternate implementation would mix the two voltages to provide a single output similar to the example graphed in FIG. 5 (see FIGS. 6 and 7, for example).

Figure 5:
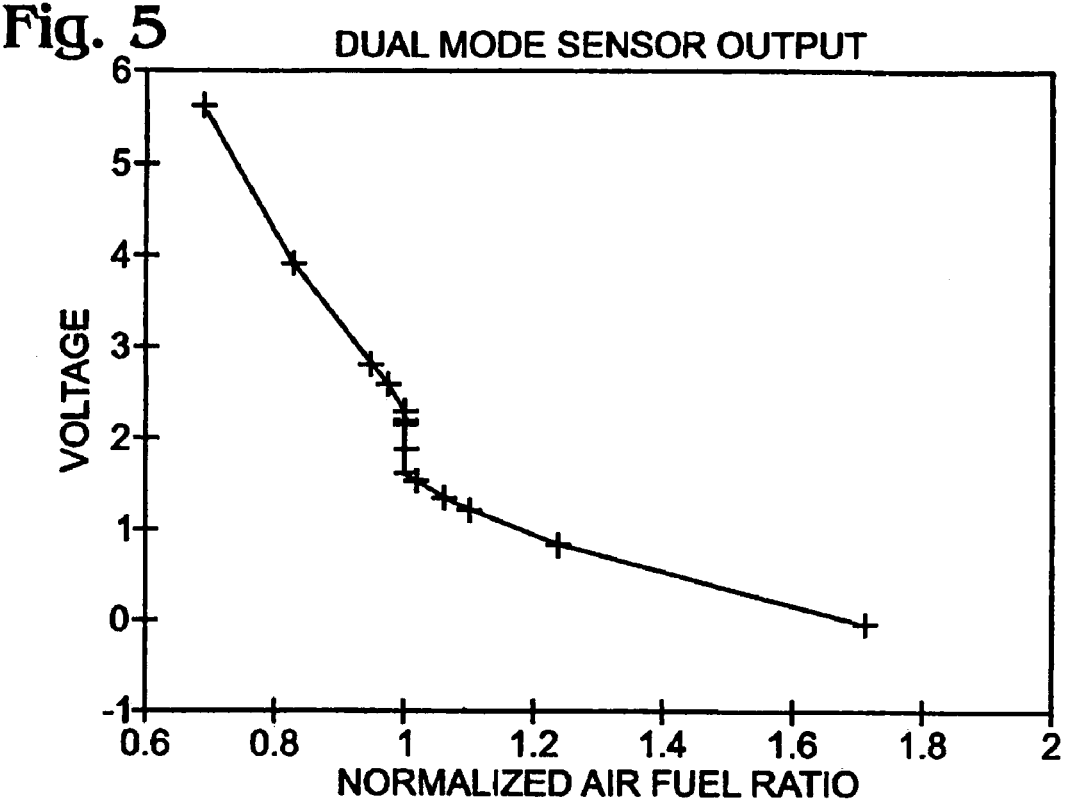
FIG. 5 is a graph illustrating experimental data.

It can be seen from FIG. 5 that the output from the sensor, when controlled according to this invention, provides both the accurate, high gain signal near stoichiometry and the wide range air-fuel ratio output (such as that normally obtained from the UEGO sensor).

In this way, it is possible to control a dual cell UEGO sensor to provide a HEGO like signal at stoichiometry, while at the same time to provide a UEGO like signal at air-fuel ratios away from stoichiometry by turning the pumping current off at stoichiometry and providing a signal that blends the output of both the reference and pumping circuit.

As such, in one example, only a single signal is advantageously used to provide both high resolution and wide range air-fuel signal. Such an approach is advantageous relative to a system that, for example, uses two signals to provide such information. For example, the single signal approach requires fewer wires between the sensor and controller, as well as fewer A/D converters and less potential degradation.

Figure 6:
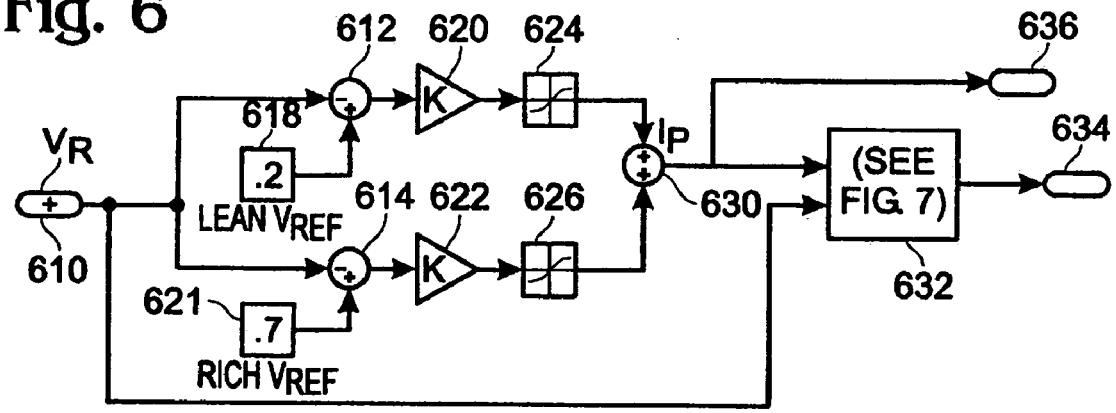
FIGS. 6, 7, 8 and 9 are a high level flowchart and block diagrams of control routines.

The circuits described above with regard to FIG. 4 show one aspect of the signal and sensor 140. However, other approaches can be used, such as digital signal processing. To illustrate the general approach used, regardless of whether digital or analog circuits are used in the implementation, FIG. 6 shows a block diagram of example signal conditioning that can be used. Specifically, the voltage reference signal 610 is shown leading to a summation 612 and 614. At summation 612, the signal $V_r$ is compared to a lower lean voltage reference of 0.2 (block 618). This difference is sent to a high gain amplifier (k) at 620. Likewise, the reference voltage is also compared to an upper rich voltage reference of 0.7 (621), the difference of which is also sent to an amplifier of gain (k) at 622. The output of gain 620 is fed to the saturation block 624 which limits the pumping current at positive values. Similarly, the output of gain 622 is fed to saturation block 626 which limits pumping current to negative values. The sum of the outputs of block 624 and 626 are fed to a summation 630, the output of which is the pumping current ($i_p$). Then, if desired, the pumping current and voltage reference are sent to block 632 to be modified to produce a single output ($V_{out}$). Alternatively, or in addition, the pumping current can be output at block 636.

This block diagram of FIG. 6 has three modes which are determined based on the reference voltage ($V_r$).

If the reference cell output is less than 0.2, the upper portion of the control circuit will generate a positive pumping current and control the reference cell to 0.2. The saturation block 624 blocks the output of the lower portion of the circuit. Conversely when the reference cell voltage reaches 0.7 volts, the lower portion of the circuit will generate negative pumping currents to control the reference cell voltage. When the reference cell voltage is between 0.2 and 0.7, the outputs from both of the controllers will be blocked by their saturation blocks and no pumping current will flow; yet, the reference voltage will be driven by the oxygen concentration of the measurement exhaust gas.

Figure 7:
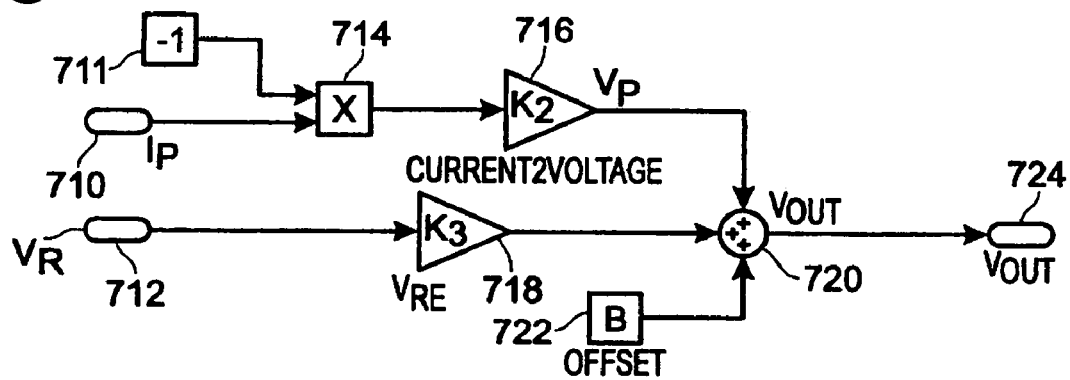

As indicated above, two output signals can be used ($V_p$ and $V_r$) to provide a high gain output signal ($V_r$) and a wide range output signal ($V_p$). However, in an alternative embodiment, these two separate outputs can be combined into a single output signal as indicated by block 632 in FIG. 6, which is now described with regard to FIG. 7. The block diagram of FIG. 7 shows how the two inputs (pumping current 710 and reference voltage 712) are combined to a single output voltage (724). Specifically, the pumping current is inverted in block 714 by multiplying it by negative one from block 711. Then, this signal is sent to a gain ($k_2$) in block 716 to produce a pumping voltage ($V_p$). Likewise, the reference voltage is sent to a gain at block 718 of $k_3$ which is indicated as $V_{re}$. The outputs of blocks 716 and 718 are then summed at summation 720, along with an opposite voltage (B from block 722). The output of the summation is then sent to the output at block 724.

Thus, while the reference cell voltage and a voltage that correlates to the pumping current could be output independently, in this example the above circuit combines them into a single output to reduce the number of inputs circuits required to read the sensor output.

Figure 8:
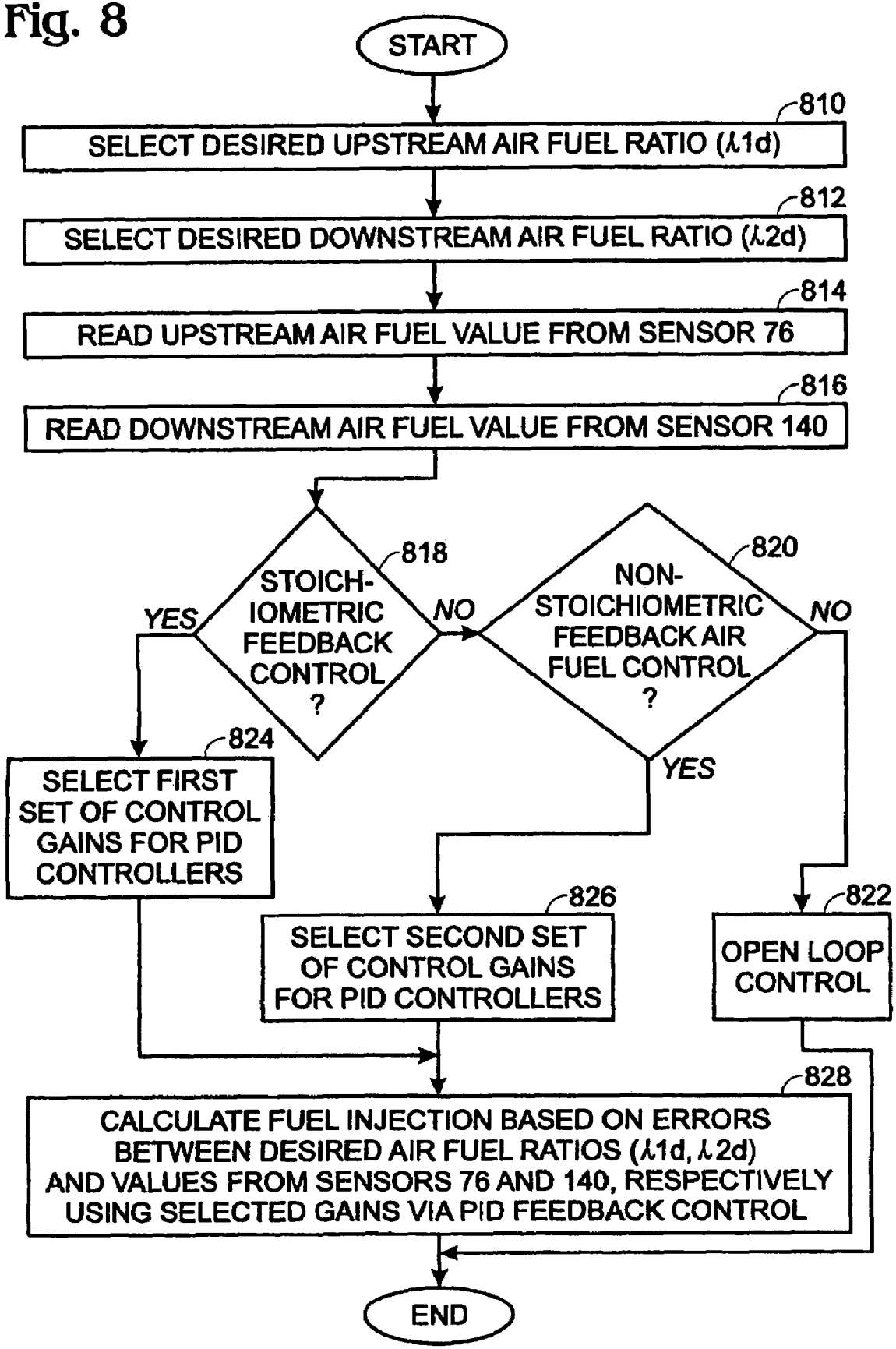

Referring now to FIG. 8, a routine is described for adjusting fuel injection using feedback control in the information from the exhaust gas sensors 76 and 140. First, in step 810, the routine selects a desired upstream air-fuel ratio ($\lambda_{1d}$). Next, in step 812, the routine selects a desired downstream air-fuel ratio ($\lambda_{2d}$). Next, in step 814, the routine reads the upstream air-fuel value from sensor 76, and in step 816, the routine reads the downstream air-fuel value from a sensor 140 as described above herein. Then, in step 818, the routine determines whether stoichiometric feedback control is active. In other words, the routine determines whether closed-loop feedback control about stoichiometric air-fuel ratio is selected. When the answer to step 818 is no, the routine continues to step 820. In step 820, the routine determines whether non-stoichiometric feedback air-fuel control is selected. For example, the routine can determine whether rich air-fuel ratio control or lean air-fuel ratio control is selected at a desired rich or lean air-fuel ratio. When the answer to step 820 is no, the routine goes to step 822 and carries out open loop air-fuel ratio control independent of sensors 76 and 140.

Alternatively, when the answer to step 818 is yes, the routine continues to step 824 to select a first set of control gains for PID controllers used to feedback control both the downstream and upstream air-fuel ratio to the desired values. Alternatively, when the answer to step 820 is yes, the routine continues to step 826 to select a second set of gains for the PID controllers. In other words, a first set of control gains is used for the high gain sensor output of sensor 140 in the stoichiometric region, whereas a second set of control gains is used for the wide range signal output from sensor 140 away from stoichiometry.

Then, in step 828, the routine calculates a desired fuel injection amount based on errors between the desired air-fuel ratios and the values from sensors 76 and 140, respectively. This fuel injection calculation is determined using the selected gains for the current operating conditions in a proportional interval derivative (PID) feedback control system.

In this way, it is possible to advantageously utilize the multi-purpose signal output from sensor 140, as shown by FIG. 3 or 4, for example.

Note that while the above approach modifies the desired fuel injection amount to control the air fuel ratio, alternative approaches can be used. For example, when using an electronically controlled throttle plate (e.g., via an electric motor controlled by the controller) it can be desirable to modify the air flow to control air fuel ratio. In other words, rather than scheduling an air flow as a function of the driver demand (and setting fuel to achieve the desired air fuel ratio), one can schedule a fuel flow based on the driver demand (or other engine torque request) and calculate the required air to provide a desired air-fuel ratio. Further, feedback can be used to modify the desired airflow to obtain the target air fuel ratio using information from the sensor described above. Such an approach can provide accurate air-fuel ratio control with less torque disturbances. Still another alternative approach would be to modify both air and fuel based on the sensor.

Figure 9:
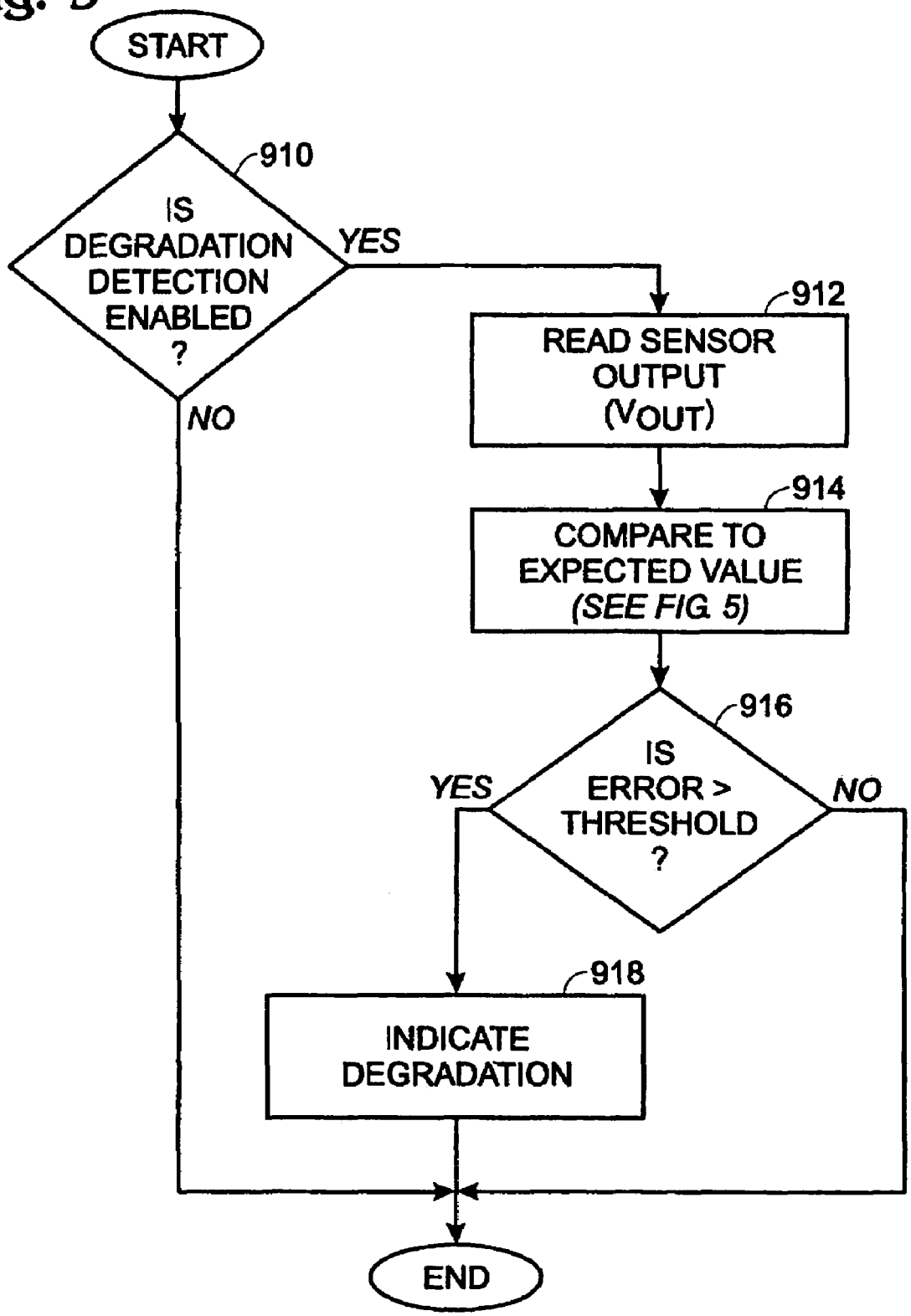

Referring now to FIG. 9, a routine for determining degradation of sensor 140 is described. First, in step 910, the routine determines whether degradation detection is enabled. For example, degradation detection of sensor 140 can be enabled based on a combination or one of the following: whether the time since engine start is greater than a predetermined value, whether engine cooling temperature is greater than a determined value, whether the engine has traversed a variety of air-fuel ratios across the range of sensor 140, or various other conditions. When the answer to step 910 is yes, the routine continues to step 912. In step 912, the routine reads the sensor output of sensor 140 ($V_{out}$). Then, in step 914, the routine compares the read value to the expected value as would be determined from stored information such as that illustrated in FIG. 5. Then, in step 916, the routine determines whether error between the expected and read threshold value is greater than a threshold value. Note that, rather than a single comparison, a multitude of comparisons over a variety of air-fuel ratios representing the range of air-fuel ratios over which sensor 140 can be used. When the answer to step 916 is yes, the routine continues to step 918 to indicate the degradation, such as via an indicator lamp to the driver.

Note that, in the event the pumping circuit degrades (but the reference cell is still operating appropriately, failed, the sensor can still provide a limited output similar to a HEGO, which can be used during default operation. If, however, the pumping call or circuit degrades, default operation is selected to be carried out with open-loop fuel control.

In this way, it is possible to determine degradation of a sensor having an output that has both a high gain near stoichiometry, and a wide range air-fuel ratio output, as well as schedule default operation.

Figure 10:
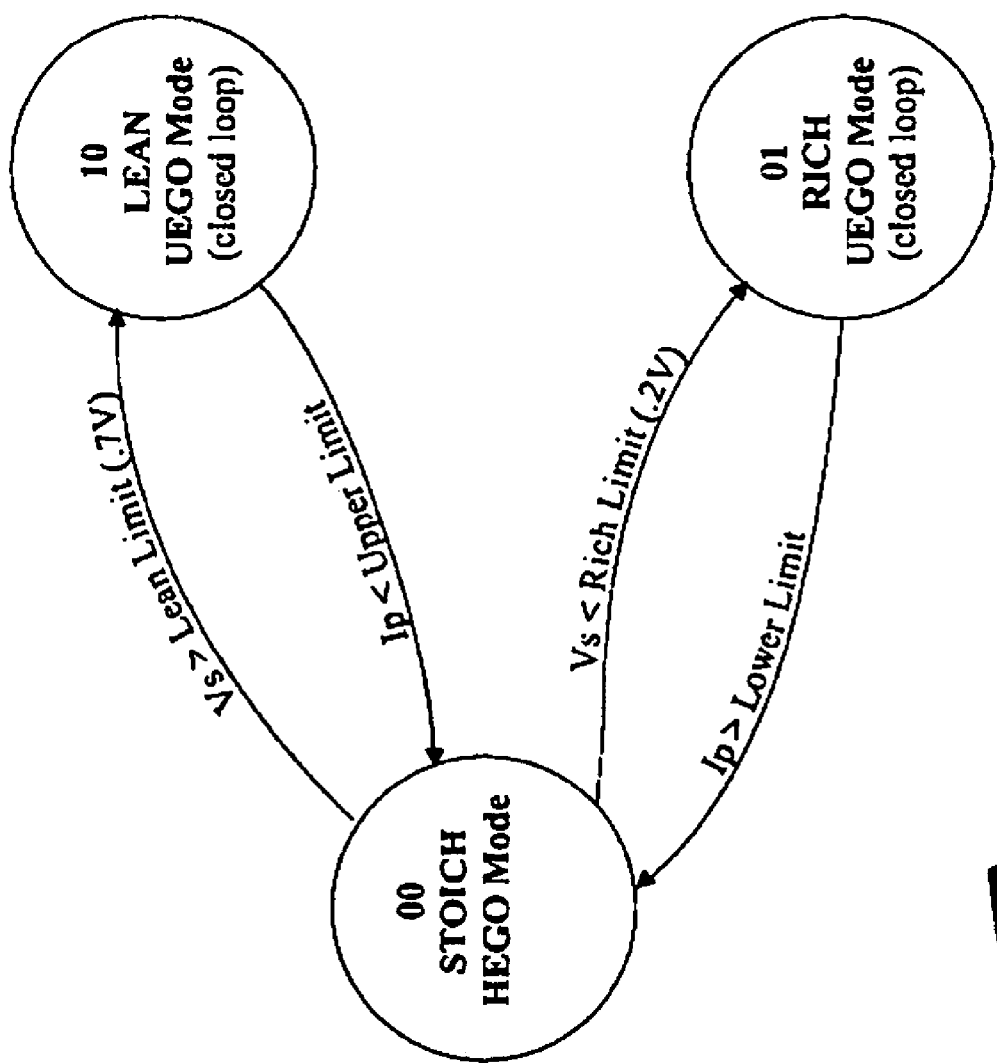
FIG. 10 is state diagram of control logic.

Referring now to FIG. 10, a state diagram of control logic for use with a sensor of the type as sensor 140 and/or 1140 is shown. Specifically, the figures shows how engine modes, in this example air-fuel ratio control modes, may be changed depending on the output of the sensor. Mode 00 includes open loop (and/or closed loop) stoichiometric feedback control, which can include where the engine air-fuel ratio is ramped until a "switch" of the sensor is detected, at which point the air-fuel ratio is adjusted to jump and ramp in the opposite direction. In this way, oscillation about stoichiometry can be achieved. Alternatively, the air-fuel ratio can be adjusted independent of the sensor output.

Mode 10 includes lean closed loop feedback air-fuel ratio control at a desired lean air-fuel ratio value, where feedback is obtained from sensor 140 providing an indication of the degree of leanness in the exhaust gas. The control transitions from Mode 00 to Mode 10 when the sensor voltage (Vs) is greater than a lean limit value (0.7 volts in this example). Further, the control transitions from Mode 10 to Mode 00 with the pump cell current (Ip) is less than a threshold value (designated Upper Limit in this example).

Mode 01 includes rich closed loop feedback air-fuel ratio control at a desired rich air-fuel ratio value, where feedback is obtained from sensor 140 providing an indication of the degree of richness in the exhaust gas. The control transitions from Mode 00 to Mode 01 when the sensor voltage (Vs) is less than a rich limit value (0.2 volts in this example). Further, the control transitions from Mode 01 to Mode 00 with the pump cell current (Ip) is greater than a threshold value (designated Lower Limit in this example).

In this alternative method for the sensor 1140 for detecting air-fuel ratios, Mode 00 may be an open-loop, "HEGO-like" mode, using only the voltage reference cell to detect air-fuel ratios near stoichiometry, with greater sensitivity. And Mode 10 can use the sensor in a lean feedback manner ("UEGO-like", with the pumping cell enabled, to detect air-fuel ratios away from stoichiometry.

FIG. 10 thus illustrates one of several possible sequences of operation. When control logic determines that the sensor is ready for operation (such as based on a time since engine start, or based on the sensor response), the sensor goes into Mode 00. The output from the circuit can be either a fixed output or the reference cell voltage (Vs) passed through an amplifier and connected to the output terminal.

If the air-fuel mixture becomes lean, Vs quickly exceeds 0.7 volts, the comparator labeled "Vs > Lean Limit" sends an output to the dual mode control logic. The pumping cell is then enabled, Vs is held at 0.45 volts, and the pumping cell current (Ip), as measured by the sense resistor (Rs), is passed through an amplifier(s) to the output terminal. The sensor is now in the Lean "UEGO-like" state (Mode 01).

If the air-fuel mixture then becomes rich enough, Ip will decrease to a value that causes the comparator "Ip < Upper Limit" to send an output to the dual mode control logic. Ip is disabled and the sensor is in Mode 00 again.

If the mixture continues to become richer, Vs decreases below 0.2 volts, the comparator "Vs < Rich Limit" sends an output to the dual mode control logic. Ip is enabled, Vs is held at 0.45 volts, and Ip, measured across Rs, is passed through amplifier(s) to the output terminal. The sensor is now in the Rich "UEGO-like" state (Mode 01).

If the mixture then becomes lean enough, Ip will increase to a value that causes comparator "Ip > Lower Limit" to send an output to the dual mode control logic. Ip is disabled and the sensor is in Mode 00 again.

The paragraphs above show the state transitions that can occur, as illustrated by the attached logic state diagram. The specific values for Ip Lower Limit or Ip Upper Limit can be selected as desired based on the application. The optimum values can be determined empirically.

Figure 11:
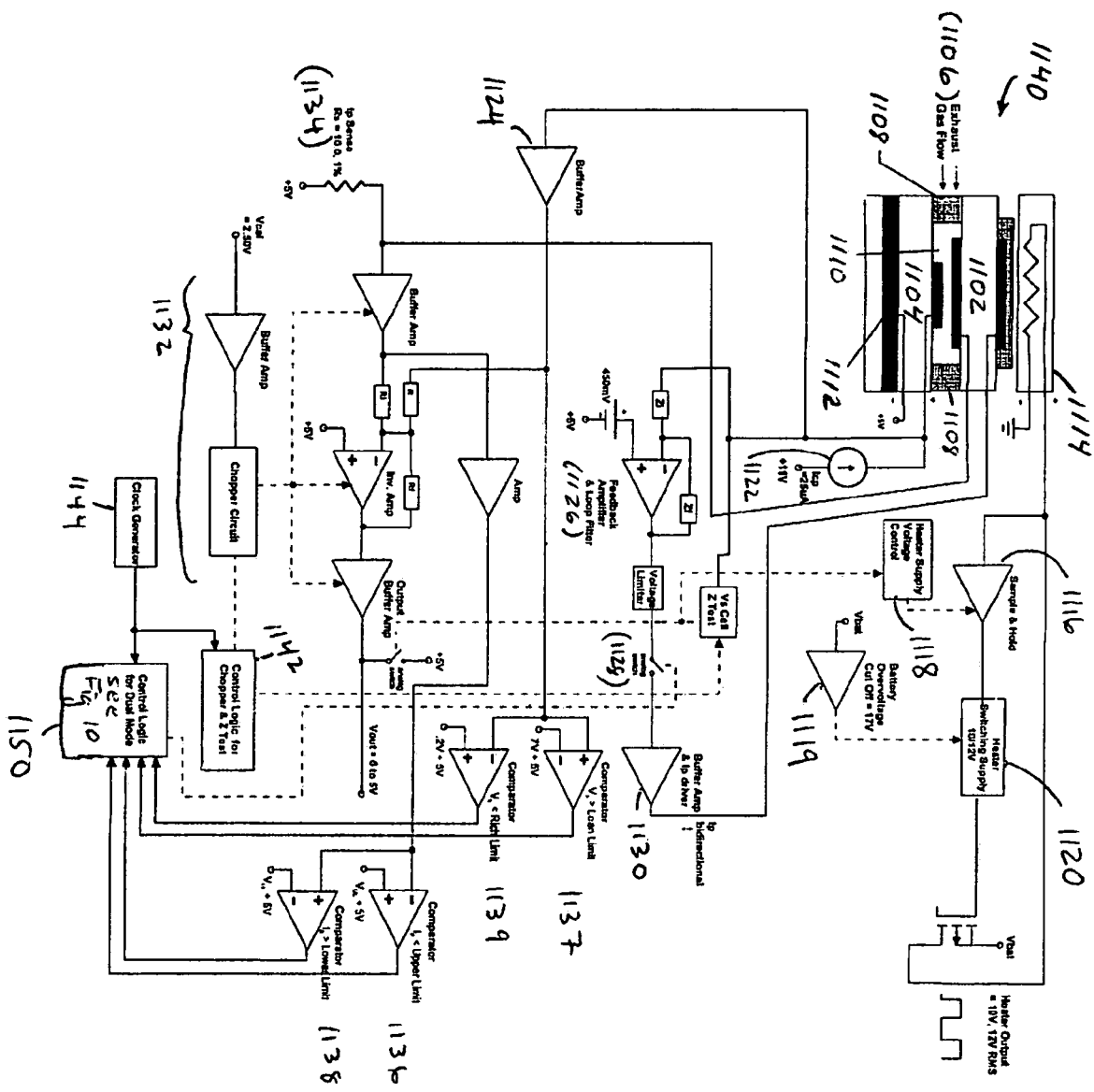
FIG. 11 is an alternative embodiment of control circuitry and an exhaust gas sensor.

Referring now to FIG. 11, an alternative sensor and circuit configuration is shown, optionally for use with the logic of FIG. 10. In this alternative configuration, additional components and circuitry have been added to provide additional functionality.

Specifically, this alternative embodiment shows sensor 1140 with a pump current cell 1102 and a voltage reference cell 1104. The figure also identifies the direction of exhaust gas flow at 1106 and the porous diffusion passage(s) at 1108. Gas detection cavity 1110 and O2 reference electrode 1112 are also indicated on the sensor. Further, a ceramic heater 1114 is shown for heating the sensor 1140.

The output of the circuits is shown coupled to various amplifiers and circuitry. Specifically, the output voltage to the heater 1114 is fed to a sample and hold amplifier 1116, receiving command controls from a heater voltage supply circuit 1118 (which can be controlled via control logic to be selectively activated based on engine and exhaust gas operating conditions). In this example, control signals are generated from the control logic at 1150, which may includes the logic of FIG. 10, as well as other control logic. A battery overvoltage amplifier 1119 is also shown coupled to the heater supply 1120, to disable the voltage sent to heater 1114.

Continuing with FIG. 11, a current supply 1122 is shown coupled to the reference electrodes 1112. Further, the reference cell is also coupled to buffer amplifier 1124 and feedback amplifier and Loop filter 1126, along with analog switch 1128 and amplifier 1130 to provide bidirectional pump current (Ip).

Another set of amplifiers, including a chopper circuit and resistors, 1132, is shown for measuring the pump current via resistor Rs at 1134. Comparators 1136, 1137, 1138, and 1139 are also shown for providing control input signal to block 1150. Also, control logic for the chopper circuit, and test logic, may be contained in block 1142. Both block 1150 and 1142 receive input from a clock generator (1144).

In general, the above circuitry can be referred to as: heater control, feedback circuitry for stable operation of the sensor, Ip driver, Icp for controlled leakage into Vs, chopper amplifier to minimize output errors and drift, and Z test to determine cell readiness for operation.

This concludes the description of the invention. The reading of it by those skilled in the art would bring to mind many alterations and modifications without departing from the spirit and the scope of the invention. Accordingly, it is intended that the scope of the invention be defined by the following claims. Further, the following claims particularly point out certain combinations and subcombinations regarded as novel and nonobvious. These claims may refer to "an" element or "a first" element or the equivalent thereof. Such claims should be understood to include incorporation of one or more such elements, neither requiring nor excluding two or more such elements. Other combinations and subcombinations of features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

We claim:

1. A system comprising:
   an oxygen sensor having a pumping cell and a reference cell and producing an output voltage, the reference cell including an air-filled chamber and producing a reference voltage;
   electronics configured to measure the reference voltage, and further configured to turn off a current to the pumping cell to allow the reference voltage to float within a voltage range, and to apply the current to the pumping cell if the reference voltage is outside the voltage range;
   the electronics including first and second amplifiers arranged in parallel and configured to supply the current to the pumping cell, the first amplifier applying the current to the pumping cell in a first direction and the second amplifier applying current to the pumping cell opposite the first direction;
   the output voltage based on the reference voltage and on the current to the pumping cell.

2. The system of claim 1, the electronics further comprising a first and second feedback loop,
   the first feedback loop including the first amplifier and a first diode; and
   the second feedback loop including the second amplifier and a second diode.

3. The system of claim 2, wherein said current flows through the first diode in a first direction and through the second diode opposite the first direction.

4. The system of claim 1, wherein the electronics includes a storage medium storing digital code.

5. The system of claim 1, wherein the electronics maintains the reference voltage at limits of the voltage range by increasing said current in the first direction if the reference voltage is at a first limit, and increasing said current opposite the first direction if the reference voltage is at a second limit.

6. A system comprising:
   an oxygen sensor having a pumping cell and a reference cell and producing an output voltage, the reference cell including an air-filled chamber and producing a reference voltage;
   electronics configured to measure the reference voltage, to apply a current to the pumping cell in a first direction to prevent the reference voltage from increasing above a first voltage limit, and to apply a current to the pumping cell opposite the first direction to prevent the reference voltage from decreasing below a second voltage limit;
   the electronics including first and second amplifiers arranged in parallel to supply the current to the pumping cell, the first amplifier applying the current to the pumping cell in a first direction and the second amplifier applying the current to the pumping cell opposite the first direction;
   the output voltage based on the reference voltage and on the current to the pumping cell.

7. The sensor of claim 6 wherein the electronics is further configured to apply current to the pumping cell to prevent the reference voltage from increasing above the first voltage limit, but to allow the reference voltage to decrease below the first voltage limit without applying the current to the pumping cell.

8. The sensor of claim 7 wherein the electronics is further configured to apply current to the pumping cell to prevent the reference voltage from decreasing below the second voltage limit, but to allow the reference voltage to increase above the second voltage limit without applying the current to the pumping cell.

9. The sensor of claim 8 wherein the electronics is further configured to output a signal responsive to both the current in the pumping cell and the reference voltage.

* * * * *